United States Patent
Werner

(10) Patent No.: US 9,011,424 B2
(45) Date of Patent: Apr. 21, 2015

(54) METHOD AND DEVICE FOR OPTIMIZED COAGULATION OF BIOLOGICAL TISSUE

(75) Inventor: Erich Werner, Wannweil (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 315 days.

(21) Appl. No.: 13/526,638

(22) Filed: Jun. 19, 2012

(65) Prior Publication Data

US 2013/0006237 A1    Jan. 3, 2013

(30) Foreign Application Priority Data

Jun. 30, 2011    (EP) .................................... 11172084

(51) Int. Cl.
*A61B 18/18*    (2006.01)
*A61B 18/12*    (2006.01)
*A61B 18/00*    (2006.01)

(52) U.S. Cl.
CPC ... *A61B 18/1206* (2013.01); *A61B 2018/00672* (2013.01); *A61B 2018/00678* (2013.01); *A61B 2018/00702* (2013.01); *A61B 2018/00779* (2013.01); *A61B 2018/00875* (2013.01)

(58) Field of Classification Search
USPC .......................................................... 606/40
See application file for complete search history.

(56) References Cited

U.S. PATENT DOCUMENTS

| | | | |
|---|---|---|---|
| 6,436,096 B1 * | 8/2002 | Hareyama | 606/34 |
| 2002/0151884 A1 | 10/2002 | Hoey et al. | |
| 2003/0158551 A1 | 8/2003 | Paton et al. | |
| 2007/0293858 A1 * | 12/2007 | Fischer | 606/51 |
| 2008/0147057 A1 * | 6/2008 | Eisele | 606/34 |
| 2011/0077630 A1 * | 3/2011 | Tanaka et al. | 606/29 |

FOREIGN PATENT DOCUMENTS

| | | |
|---|---|---|
| DE | 10 2004 041 681 A1 | 2/2006 |
| EP | 1886636 | 2/2008 |
| EP | 2213255 | 8/2010 |
| JP | 2010-158526 A | 7/2010 |

* cited by examiner

*Primary Examiner* — Robert N Wieland
(74) *Attorney, Agent, or Firm* — Dickstein Shapiro LLP

(57) ABSTRACT

Maximum HF current is initially introduced into tissue at a pre-specified maximum coagulation voltage. In this initial state, the tissue behaves in accordance with Ohm's law and can take up the maximum energy per unit of time. After the tissue has changed from an initial state to a state in which the tissue impedance or resistance is voltage-dependent, the HF parameters are selected such that the maximum possible energy input per unit of time is set.

18 Claims, 2 Drawing Sheets

METHOD AND DEVICE FOR OPTIMIZED COAGULATION OF BIOLOGICAL TISSUE

RELATED APPLICATION

This application claims priority to European patent application EP 11 172 084.3, filed on Jun. 30, 2011, which is hereby incorporated by reference in its entirety.

TECHNICAL FIELD

Embodiments of the invention relate to a method and a system for the coagulation of biological tissue by introducing electrical current into said tissue.

BACKGROUND

Electrical tissue coagulation has been found to be a proven means of reducing unwanted tissue volumes in surgical practice. High-frequency (HF) electric current is used for coagulation. Different methods exist for its determination.

EP 1 886 636 A1 discloses such a method. It is based on first applying a constant electrical signal (e.g., a constant voltage) to the tissue to ascertain its initial resistance. This phase can last 2 to 3 seconds, for example, and precedes the actual electrosurgical treatment. Other constant parameters such as constant power, constant current or energy, are stipulated for measuring the initial tissue resistance instead of using a constant voltage. After commencing treatment, the initial tissue resistance, the drop in impedance which then takes place, the impedance minimum and the first rise in impedance, are recorded and analyzed. The values of these variables provide information on the conditions at the electrodes and on the tissue type, as well as the moisture level thereof. Treatment parameters are specified accordingly, for example, in terms of the duration of treatment or the energy to be applied. A reference table is used for this purpose and is stored in a memory. A microcontroller uses the treatment values obtained from the reference table and adopts these as a basis for the subsequent treatment.

Surgical procedures are often time-critical. It is therefore desirable to conclude coagulation processes in the shortest time possible while ensuring high quality and reproducibility.

SUMMARY

On that basis, an object of the embodiments of the invention is to provide an improved coagulation method and an improved coagulation device.

The method in accordance with the embodiments of the invention commences with the application of a coagulation-inducing HF voltage to the biological tissue to initiate coagulation without a preceding measurement phase. In the simplest case, the specified HF voltage can be a constant voltage. A specified variation in voltage over time that can, for example, comprise at least one rise in voltage and/or at least one fall in voltage, can also be used as the specific HF voltage (e.g., the specific HF voltage can follow a pre-defined voltage curve).

As mentioned above, a pre-defined constant HF voltage can be used as the initially applied specific voltage. This has a maximum peak value of preferably 200V, which avoids the generation of sparks and development of a plasma, and thereby avoids rapid desiccation of the tissue.

The variation in electrical tissue resistance is monitored during the application of the specific HF voltage. Depending on the embodiment, the tissue resistance for all of the variants described below is the ohmic resistance of the tissue, the complex apparent resistance of the tissue, the value of the complex apparent resistance, the real component of tissue impedance or the imaginary component of the tissue resistance.

Monitoring of the tissue resistance can be ongoing (i.e., continuously) or, for example, at intervals (e.g., continually repeated). The time intervals can be chosen to be constant or varying as required. They can be e.g., a few milliseconds.

If a rising trend of the tissue resistance is established, then the HF voltage is regulated such that the electrical tissue resistance satisfies certain criteria. These specified criteria can, for example, be a desired time course, maintenance of a constant value or just the criterion that the tissue resistance does not exceed a certain maximum value or that it is within a specified range. These measures enable a high defined energy input to be achieved within a short time, without the tissue drying out prematurely. A high quality rapid coagulation is achieved.

The specification of a certain large energy input into the tissue ensures that a correspondingly large coagulation volume is attained, wherein adhesion of the tissue to the electrode of the surgical instrument or desiccation of the tissue can be reliably ruled out. Restricting the tissue resistance to values that are not too high, i.e., preventing a rise in tissue resistance, affords reliable protection against desiccation of tissue and its adherence to the electrode. The embodiments of the invention therefore enable reproducible high quality coagulation results with a short treatment time.

Monitoring of the variation in electrical tissue resistance can be carried out by the ongoing determination of resistance and comparison with a limit value, a reference value, a tolerance band or the like. The comparative value can be a fixed specified value, a previously measured value or an average value that is formed continuously, for example from the last measured values. A rising trend in the tissue resistance can be established if, for example, the current value of the tissue resistance exceeds the comparative value. In contrast to the specification of rigid limits for tissue resistance, this approach permits an adaption to individual tissue characteristics.

The desired tissue resistance used can also be a minimum value of the tissue resistance established over the course of the change in resistance or a value specified in a fixed ratio thereto. For example, a fixed percentage increase of, for example, 20% can be added to the measured minimum tissue resistance and the resistance value so obtained can be used as the setpoint or limit value for the tissue resistance, which is used as the setpoint for the setting of the tissue resistance. It is also possible to use a fixed time course for the tissue resistance instead of a specified setpoint.

It is possible to continue the coagulation process on the basis of the regulation of the tissue resistance up to a physiological equilibrium at the coagulation limit. This enables very large tissue volumes to be coagulated. However, it is possible to measure the energy introduced into the tissue and to limit it to a maximum energy quantity. Since, with the method in accordance with the embodiments of the invention, the volume coagulated is proportional in a very good approximation to the energy input, the volume coagulated can be influenced by the latter. For example, the surgeon can specify the volume to be coagulated as an input parameter on a medical apparatus and then work blindly to a certain extent. This is advantageous, particularly if greater volumes and greater tissue depths have to be coagulated. By its very nature, the coagulation depth reached can only be recognized by the surgeon with difficulty. The limiting of the introduced energy helps the surgeon here.

After the application of the fixed energy quantity, the voltage applied at the electrode can be reduced to a minimum value that does not lead to coagulation. The voltage can be an HF voltage, an LF (low frequency) voltage, an AC voltage of any desired waveform or a DC voltage. A renewed contact between the instrument and tissue can be recognized by monitoring of the current flow, and a new treatment can be initiated.

BRIEF DESCRIPTION OF THE DRAWINGS

Hereinafter, exemplary embodiments of the invention are explained in greater detail with reference to drawings, in which.

DETAILED DESCRIPTION

Figure 1:
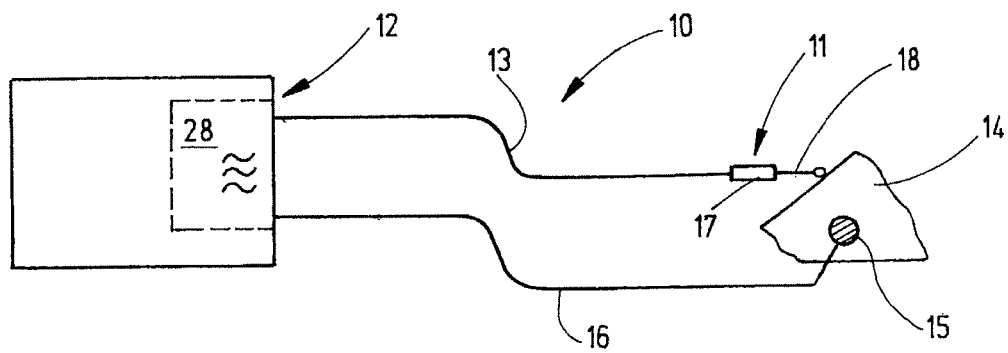
FIG. 1 is a schematic representation of an electrosurgical unit and a corresponding instrument for the coagulation of biological tissue.

FIG. 1 shows a device 10 for the electrosurgical treatment of human or animal patients comprising a surgical instrument 11 and a unit 12 for supplying high-frequency current to said instrument 11. The instrument 11 and unit 12 are inter-connected by a line 13. The instrument 11 is used for zone-by-zone coagulation of biological tissue 14, which is connected to the unit 12 via a neutral electrode 15 and a corresponding neutral line 16. The biological tissue 14 shown in FIG. 1 symbolizes part of a patient.

The unit 12 comprises an HF generator 28 for generating a HF voltage of sufficient amplitude (for example, up to several hundred volts) and a control device (not shown) for the HF generator 28. Operating elements and display elements, which can be provided on the unit 12 to regulate and control the operation of the device 10 are not shown in detail in FIG. 1.

Figure 2:
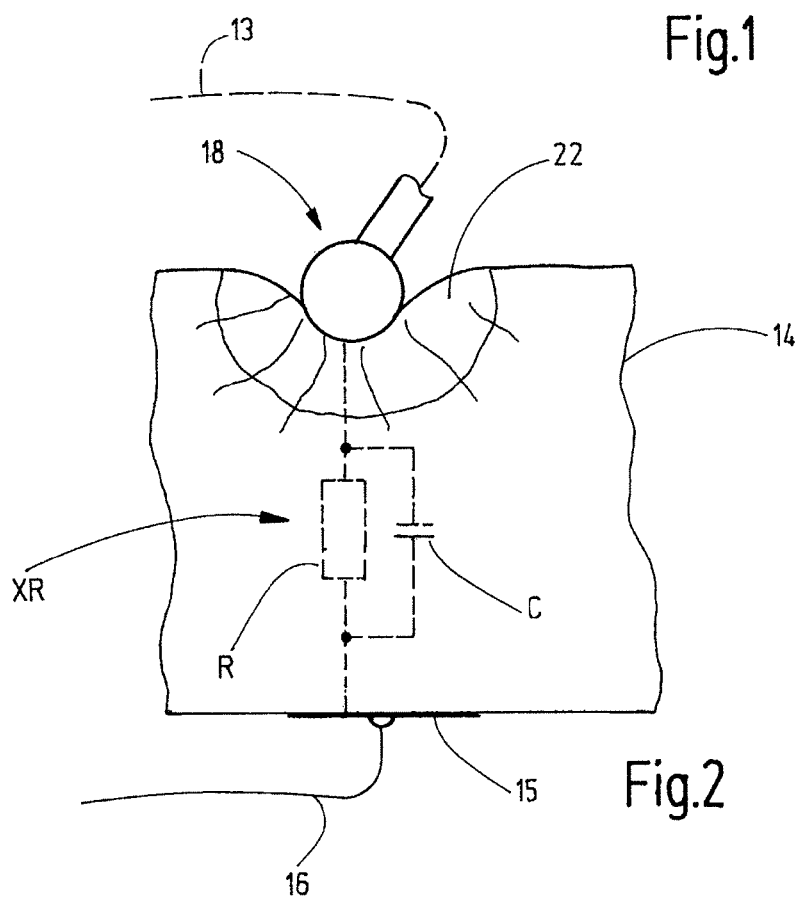
FIG. 2 illustrates the biological tissue during coagulation, shown symbolically.

The instrument 11 comprises an electrically isolating handle 17 and an electrically conductive electrode 18 for direct effect on the tissue 14. FIG. 2 illustrates the tissue 14 and the electrode 18 interacting with the tissue 14. The electrode 18 is shown in the FIG. 2 example as a ball electrode for illustration purposes only; it should be appreciated that any other suitable electrode shape can be used, particularly a plate, knife, loop or the like.

The biological tissue 14 forms a path that can conduct current between the electrode 18 and the neutral electrode 15, with the impedance of said path being designated as the tissue resistance XR. This tissue resistance XR exhibits a usually dominating ohmic component in the form of an ohmic resistance R. In addition, the tissue resistance XR can comprise reactive components, which are illustrated in FIG. 2 by a capacitance C and by a capacitor (shown in dashed lines). This tissue resistance XR/tissue impedance can additionally comprise inductive portions, which must be understood as being in series with the ohmic resistance R. The following description refers in general to the tissue resistance XR. The description refers both to embodiments in which the tissue resistance XR is understood to comprise the complex resistance formed from the ohmic resistance R and the capacitance C, as well as to embodiments in which the tissue resistance XR comprises only the ohmic resistance R, the capacitance C or a variable formed from both R and C that is measured, evaluated or subject to open-loop or closed-loop control, etc.

Figure 3:
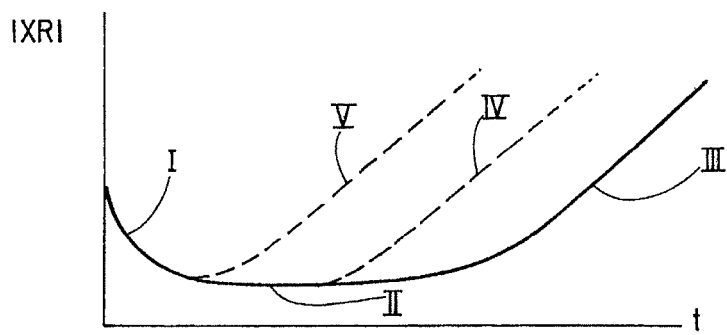
FIG. 3 illustrates the possible time-dependent changes in tissue resistance in the form of a diagram.

FIG. 3 illustrates the value of the tissue resistance XR as a function of the time over which HF power is introduced into the biological tissue 14. As curve I shows, the tissue resistance initially falls relatively fast and reaches a low value within the range of curve II. Continued energy input leads to denaturation and drying out of the tissue, resulting in a rise in tissue resistance as shown in curve III. As the dashed curves IV and V illustrate, this resistance increase can also occur at an earlier point in time, for example, when more power is introduced into the tissue 14 as a result of applying a higher HF voltage.

Figure 4:
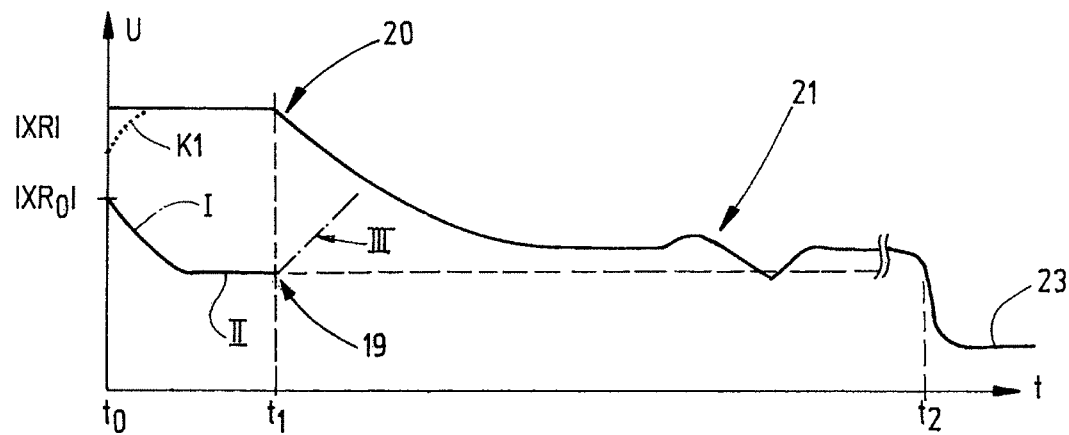
FIG. 4 is a plot of the tissue resistance and applied HF voltage with the method in accordance with the embodiments of the invention.

FIG. 4 illustrates the time variation in tissue resistance XR and the associated change in the peak value of the HF voltage at the electrode 18 opposite the neutral electrode 15 when the method in accordance with the embodiments of the invention is applied.

The coagulation process of a zone or volume 22 (FIG. 2) of the biological tissue 14 commences at time t0. At this time, the electrode 18 is in contact with the tissue 14 and a specific HF voltage is applied at the electrode 18; there is a tissue resistance XR. This HF voltage in the present example is a sinusoidal voltage with a peak value below 200V. It should be appreciated that other voltage waveforms can be used. For example, the sinus-wave voltage can be pulsed, which leads to a crest factor (peak factor) greater than the square root of two. Aside from the constant value shown, the HF voltage can also be pre-determined in another way and can rise, for example, to a constant value after the switch-on time to, as illustrated by dotted-line curve K1. It should be appreciated that other voltage variations can also be used.

The tissue resistance XT is monitored during application of the specified HF voltage U, which is either constant or variable over time. As shown, the tissue resistance XR falls initially with curve I, then reaches curve II corresponding to a low value. The high energy input as a result of the high power of the introduced HF voltage leads to a tendency of the tissue resistance XR to immediately rise again, as shown in FIG. 4 through dashed curve III. The time at which this rise is determined is shown as time t1.

The control system for the unit 12 establishes, at time t1, that curve II of the tissue resistance XR is merging into curve III at point 19. The HF generator of the unit 12 now changes from operation with the pre-specified voltage to an operating mode in which the HF voltage U is maintained such that the tissue resistance XR does not rise, or does not rise substantially, but instead remains at least very nearly constant. The switchover in the operating mode takes place at time t1, which is recognizable from the value of the voltage at the point 20. The power output of the unit 12 is regulated such that the tissue resistance XR does not rise above its initial value |XR₀|. This prevents premature drying out of the tissue and its adherence to the electrode 18.

As already indicated, a number of variants are possible for the regulation of the tissue resistance XR. The lowest measured tissue resistance can be specified as the setpoint. The control system for the unit 12 then sets this tissue resistance. The lowest measured tissue resistance, multiplied by a given or selectable factor, can also be specified as the setpoint. The lowest measured tissue resistance, increased by a given or selectable summand, can also be specified as the setpoint. Alternatively, the initial tissue resistance $XR_0$, multiplied by a given or selectable factor (that is preferably lower than 1) can be specified as the setpoint. As a further alternative, the initial tissue resistance $XR_0$ can be specified, decreased by a given or selectable subtrahend, as the setpoint. A value calculated from several measured tissue resistance values or from a value specified in an arbitrary manner can also act as the setpoint.

In the further course, the voltage can change in accordance with the work of the surgeon within the framework of the control process, as indicated symbolically at point 21 on the voltage curve in FIG. 4. A controller, however, keeps the tissue resistance XR as constant as possible, but in all cases below a limit value. The setpoint, determined by one of the above methods, can act as this limit value.

It is possible to continue the process up to a physiological/thermal equilibrium until the surgeon has coagulated the desired maximum possible tissue volume. This allows tissue volumes that are selected in an arbitrary manner or any desired tissue volumes to be coagulated. It is, however, also possible to limit the coagulation volume. FIG. 2 illustrates the volume 22 to be coagulated in the tissue 14. The restriction of this volume 22 can be achieved by controlling and limiting the power output of the unit 12. To do so, for example, the HF power delivered during the phase between times t0 and t1, as well as that delivered thereafter, is summed (integrated). If the value of the energy delivered and ascertained in this way reaches a limit value, then the unit 12 can (at time t2) interrupt or terminate the delivery of the HF voltage, or reduce it to a low value 23 that is not physiologically effective, as shown in FIG. 4. The coagulation process is thereby terminated. However, a small direct or alternating voltage of low or high frequency is present at the electrode 18 to allow detection of whether and when the electrode 18 is again contacting biological tissue 14. Such signals can be used to turn the generator of the unit 12 on again, for example to bring about a further coagulation process according to the above model.

Figure 5:
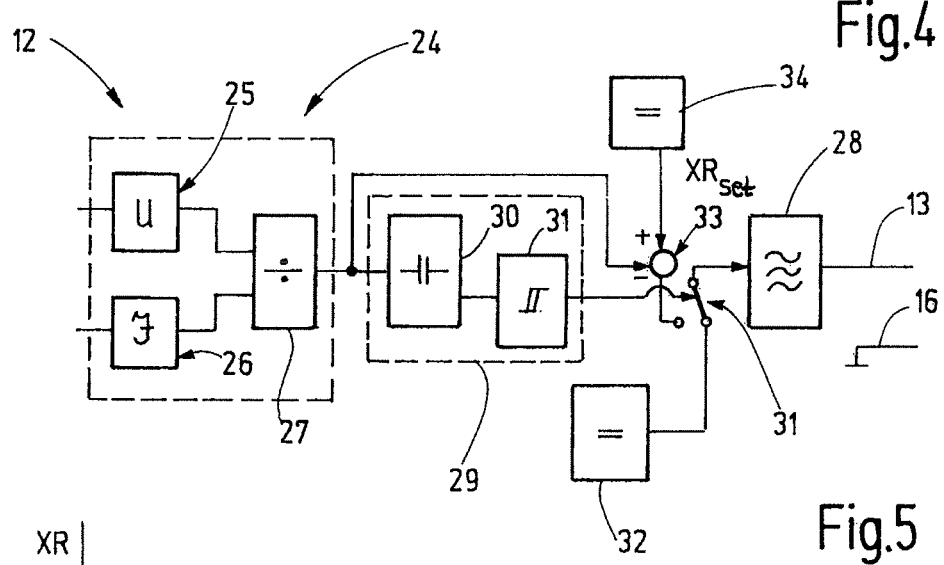
FIG. 5 is a block diagram of a part of the control system of a unit to implement the method in accordance with the embodiments of the invention.

A part of an exemplary control system for the unit 12 and for performing at least one variant of the above-described method is shown in FIG. 5. The control system contains a module 24 for recording the tissue resistance XR. This module 24 can be designed in principle in any suitable manner. The module 24 can comprise a first block 25 for recording the HF voltage at the electrode 18 and a block 26 for recording the current flowing to the electrode 18. The modules 25, 26 are, for example, correspondingly connected to line 13 leading to the instrument 11. Alternatively, module 26 can be connected to line 16. At their outputs, the modules 25, 26 supply a signal characterizing the value, the effective value or the current time value of the voltage or the current. A further block 27 forms the quotients from the signals supplied by the blocks 25, 26 and thus delivers at its output, depending on the configuration of the blocks 25, 26, a signal characterizing the complex tissue resistance XR or the ohmic component R of the tissue resistance.

The unit 12 also comprises the HF generator 28, which supplies line 13. The HF generator 28 also has a control input; control signals received at the control input determine the magnitude of the voltage delivered to line 13 at the output of the HF generator 28.

A trend recognition module 29 is connected to module 24. The trend recognition module 29 comprises, for example, a block 30 for differentiating the output signal of module 24. Block 30 delivers a positive output signal if the tissue resistance XR rises, and a negative output signal (or no output signal) if the tissue resistance XR falls. A comparator 31 transforms this signal into a switching signal. The switching signal is used to switch operation of the HF generator 28 by a switch 31 that connects the control input of the HF generator 28 to either a setpoint voltage signal supplied by block 32 or to the output signal of a subtractor 33. The latter subtracts the resistance signal supplied by module 24 from the signal supplied by block 34, which characterizes the setpoint value XRset of the tissue resistance. The deviation between the real tissue resistance XR and the setpoint value XRset, which is specified by block 34, is thus a reference variable for the control loop containing the HF generator 28.

In the simplest case, the setpoint value XRset supplied by the block 34 is a fixed and specified value that is preferably below the initial tissue resistance $XR_0$. The value XRset can, however, also be determined by block 34 and be specified, for example, by calculation. Different methods can be used to do so. For example, the setpoint value XRset can be equal to the lowest tissue resistance XR value previously measured. Alternatively, the value XRset can be a fixed sum above, or a factor higher than, the lowest tissue resistance XR previously measured. Alternatively, the setpoint value can be ascertained from previously measured values of the tissue resistance XR, for example, by comparison of several previous values of the tissue resistance with one another. For example, an average can be formed, where the average value is lower than the initial tissue resistance $XR_0$. Block 34 can also specify a desired time plot for XR, for example, in the form of a value that is constant over time or a value that varies over time. XRset can also be specified according to one of the methods given above on the basis of the initial tissue resistance $XR_0$.

Figure 6:
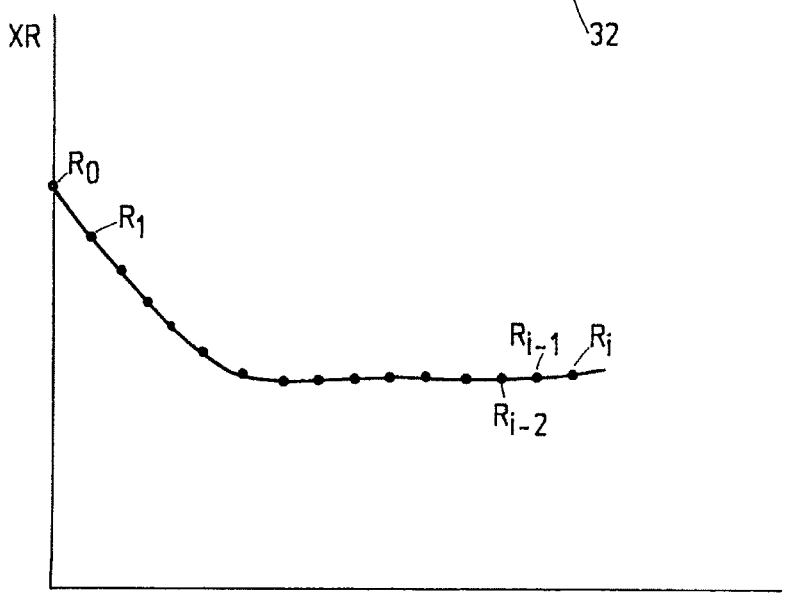
FIG. 6 is a diagram that illustrates the monitoring of the tissue resistance during time-discrete operations.

The modules, blocks, switches, subtractors and the like described above can be implemented in terms of both hardware and software technology by programs or program sections such as, for example, a program running on a microcomputer. Thus, the recording of the tissue resistance can be carried out in module 24, as described above, continuously or ongoing at repeated intervals in the manner of a scanning process, as illustrated in FIG. 6. The tissue resistance XR in FIG. 6 assumes different values over the course of time, which are characterized by dots in each case. For example, module 24 can be configured such that it compares the current resistance value $R_i$ in each case with at least one or several preceding values $R_{i-1}$, $R_{i-2}$, etc. It is also possible for an ongoing average to be formed from the preceding values $R_{i-1}$, $R_{i-2}$. If $R_i$ is greater than the current average value, then a rising trend is recognizable and the switch 31 is switched from operation with constant or pre-defined voltage (block 32) to operation with constant tissue resistance (block 34).

It is noted again that in the context of the previous description, the units and methods are considered in which between times t0 and t1 fixed specified constant HF voltages and specified HF voltage curves are used. In addition, for the previous embodiments, the units and methods are taken into consideration in which after time t1 the complex apparent resistance XR, the value of the apparent resistance XR, the ohmic component R of the tissue resistance R or another characterizing property of the tissue 14 are held constant. It is further noted that, with all the embodiments described above, an energy limitation can be provided, at which all of the energy introduced into the tissue 14 is recorded and limited to specify the volume 22 to be coagulated. Alternatively, only the amount of energy introduced into the tissue starting from time t1 is recorded and limited.

With the methods in accordance with the embodiments of the invention, the maximum HF current is initially introduced into the tissue 14 at a pre-specified and preferably constant maximum coagulation voltage (<200 Vp). In this initial state, the tissue behaves in accordance with Ohm's law and can take up the maximum energy per unit time. After the tissue has changed from an initial state to a state in which the tissue impedance or the tissue resistance XR is voltage-dependent, the HF parameters are selected such that for the new tissue state the maximum possible energy input per unit of time is set. To do so, the tissue resistance is preferably kept below the value of the initial impedance. A controller accordingly limits the tissue resistance to a value that is less than the initial impedance or to a value that is less than the lowest tissue impedance attained. An automatic termination of activation can optionally be provided when a specified input of energy is attained. This can have a value of, for example, between 10 and 500 joules. A limitation of the energy input can also be dispensed with where appropriate.

What is claimed is:

1. A method of coagulating biological tissue by introducing electrical current into said tissue using a surgical instrument, said method comprising:
    applying a specific high frequency (HF) voltage to the tissue to initiate coagulation;
    monitoring a trend of an electrical tissue resistance; and
    regulating the HF voltage to limit the electrical tissue resistance to a setpoint value when a rising trend of the tissue resistance has been determined.

2. The method of claim 1, wherein a pre-defined constant HF voltage is used as the specific HF voltage.

3. The method of claim 1, wherein the specific HF voltage has a maximum peak value of 200V.

4. The method of claim 1, wherein monitoring of the trend of the electrical tissue resistance is carried out by an ongoing determination of the current value of the tissue resistance and comparing it with a comparative value.

5. The method of claim 4, wherein the comparative value is selected from one of a fixed specified value, a previously measured value or an average value determined from a plurality of previously measured values.

6. The method of claim 4, wherein the rising trend of the tissue resistance is established if the current value exceeds the comparative value.

7. The method of claim 1, wherein a previously measured value of the tissue resistance is used as the setpoint value of the tissue resistance.

8. The method of claim 7, wherein a minimum value of the tissue resistance is used as a desired value of the tissue resistance.

9. The method of claim 1, wherein a setpoint value ascertained from previously measured values is used as the setpoint value of the tissue resistance.

10. The method of claim 9, wherein a minimum value of the tissue resistance is used as a desired value of the tissue resistance.

11. The method of claim 1, wherein a fixed setpoint value is used as a desired value of the tissue resistance.

12. The method of claim 1, wherein a fixed time curve of the value is used as a desired value of the tissue resistance.

13. The method of claim 1, wherein the energy introduced into the tissue is recorded and the HF voltage is reduced to a minimum value if a specified energy value is reached.

14. The method of claim 13, wherein recording of the energy commences as soon as the regulation of the HF voltage has commenced.

15. The method of claim 13, wherein the energy value can be specified.

16. The method of claim 13, wherein the minimum value of the HF voltage is a low value that does not lead to coagulation.

17. The method of claim 16, wherein at the minimum HF voltage the current flow is monitored to detect contact between the instrument and the tissue.

18. A device comprising an electrosurgical instrument and a unit to supply said instrument with HF voltage for coagulating biological tissue by introducing electrical current into said tissue by a method comprising:
    applying a specific high frequency (HF) voltage to the tissue to initiate coagulation;
    monitoring a trend of an electrical tissue resistance; and
    regulating the HF voltage to limit the electrical tissue resistance to a setpoint value when a rising trend of the tissue resistance has been determined.

* * * * *